United States Patent [19]

Rothstein et al.

[11] Patent Number: 5,384,259

[45] Date of Patent: Jan. 24, 1995

[54] **CONSTRUCT AND METHOD FOR EXPRESSION OF TETRACYCLINE RESISTANCE GENES IN *E. COLI***

[75] Inventors: David M. Rothstein, Pomona; Gordon G. Guay, Harriman, both of N.Y.

[73] Assignee: American Cyanamid Company, Wayne, N.J.

[21] Appl. No.: 803,635

[22] Filed: Dec. 6, 1991

[51] Int. Cl.[6] ................ C12N 1/21; C12N 15/52; C12N 15/70
[52] U.S. Cl. ................ 435/252.33; 435/320.1; 536/23.2; 536/24.1
[58] Field of Search ............... 435/320.1, 252.33, 69.1, 435/172.3; 536/27, 23.2, 24.1

[56] References Cited

PUBLICATIONS

Eckert et al. (1989), J. Bacteriol. 171(6):3557–3559.
Hillen et al. (1984), J. Mol. Biol. 172:185–201.
Watson et al. (1987), Molecular Biology of the Gene, 4th ed., Benjamin/Cummings (Menlo Park, Calif.).
Mojumdar et al. (1988), J. Bacteriol. 170(12):5522–5528.

*Primary Examiner*—Richard A. Schwartz
*Assistant Examiner*—Philip W. Carter
*Attorney, Agent, or Firm*—Estelle J. Tsevdos

[57] ABSTRACT

The present invention relates to DNA sequences useful in directing low to moderate expression of proteins in *E. coli*. The sequences are on based on modification of the repressor binding site of the tetA gene of transposon Tn10.

5 Claims, 5 Drawing Sheets

```
GTAAAGAGGTAAAATTGTTTAGTTTA    (WILD TYPE MC71)
      CG  CA                  (PT1813)
      CG  CT                  (PT1814)

SalI
      ‾‾‾‾‾
    GTCGACATGTTTAGTTT          pGG57 (tetK ATG)

SalI
      ‾‾‾‾‾
    GTCGACTTGTTTAGTTT          pGG71 (tetK TTG)
```

FIG. 2

| Plasmid | Construct | Amino Acid residues (tetK) |
|---|---|---|
| pGG57 | pCBSal containing tetK (ATG start) | 431 |
| pGG76 | pACYC184 derivative containing lacI-tetK | 431 |
| pGG77 | ▲ KpnI/SpeI from pGG76 | 196 |
| pGG84 | ▲ EcoNI from pGG76 | 161 |

FIG. 4A

CONSTRUCT AND METHOD FOR EXPRESSION OF TETRACYCLINE RESISTANCE GENES IN E. COLI

FIELD OF THE INVENTION

The present invention relates to DNA constructs adapted for low to moderate level of expression of heterologous genes in E. coli, and their use in protein expression.

BACKGROUND OF THE INVENTION

The use of microorganisms, particularly E. coli, to express foreign genes for protein production has been commonplace for many years. Since, in most cases, the purpose for using the microorganisms is to permit the production of large quantities of the protein for commercial purposes, it is usually desired to express the protein at the highest possible level. For this reason, most expression systems and the DNA constructs used therein, are specifically adapted for high level expression. However, there are situations in which low to moderate level expression is actually more desirable, or even essential, For example, overexpression of some genes is lethal. Also, in cases in which microorganisms are used as the basis for a screen to detect action of a drug against a particular gene product, a low level of expression of the protein provides for enhanced sensitivity. However, fine-tuning the level of expression is not a routine task.

As an example, it is desirable to achieve low to moderate levels of expression of the genes encoding tetracycline resistance in order to develop appropriate microorganisms for screening drugs that overcome tetracycline resistance. This resistance in the majority of microorganisms is the result of an energy-dependent efflux system (1). These efflux pumps have been analyzed in a variety of both Gram-negative and Gram-positive bacteria, and all have shown a similar secondary structure with multiple membrane spanning domains. Nonetheless comparison of the amino acid sequence of the most common Gram-negative pump, as encoded by tetA gene of E. coli from transposon Tn10, and the tetK gene from Gram-positive Staphylococcus aureus shows little identity (2). However, since these two pumps perform similar functions, it would be useful to perform studies on the tetK gene encoding the tetracycline efflux pump of S. aureus in an E. coli host, given the ease of performing genetic manipulations and biochemical studies in this system. The tetA and tetK efflux pumps are responsible for most of the clinical problems associated with tetracycline efflux. In addition, the use of isogenic strains allows better comparison of the two efflux pumps.

A problem exists, however, if the tetA or tetK genes are cloned into a standard strong expression vector. Overexpression of the tetA gene from transposon Tn10 is lethal to E. coli, e.g., if this gene is expressed in a multicopy plasmid (3, 4). In Gram-negative bacteria, regulation of the pump is mediated by the tetR gene product, a repressor, located adjacent to a common regulatory region for tetA and tetR (5, 6). Therefore, assuming expression of other genes encoding efflux pumps, such as tetK, could be achieved, it is possible that full expression would also be lethal to E. coli.

Attempts to modify the Tn10 system to permit controlled expression of the tetA from transposon Tn10gene have been made. Eckert and Beck (7) have recently cloned and expressed tetA from transposon TN10 on a multicopy plasmid in the absence of tetR, using a regulated inducible expression system. In this system when tetA is fully induced, the cells again die, perhaps due to the dissipation of the proton motive force (7); active efflux of tetracycline out of bacteria is energized by the entry of a proton into the cell, but full induction apparently leads to the loss of the proton gradient essential to the bacteria's survival. In the Eckert and Beck system, the tetA gene is regulated at the level of transcription using a regulatory region containing the strong tac promoter and the lacI gene (lactose repressor) and the lac operator site on the multicopy plasmid pCB258. Expression of the tetA gene can be regulated using different concentrations of isopropyl-B-D-thiogalactopyranoside (IPTG).

Unfortunately, the Eckert and Beck system is unsuitable for the purpose of building an optimal screening organism for detection of inhibitors of the tetracycline efflux pump. First, restriction analysis of the plasmid pCB258 indicates that one of the two tetR operator sites of the tet regulatory region remain in the plasmid adjacent to the tetA coding region. Thus, the tetA gene is regulated both by the lac repressor as well as the tetracycline repressor, if both repressors are present in the cell. The presence of both repressors causes deleterious consequences in an expression system designed for use as a screening organism. Thus, although pCB258 does permit relatively weakened expression of the tetA gene, the level of tetracycline resistance is nonetheless too high for use in screening for pump inhibitors. Moreover, there is no convenient restriction site in the appropriate region to permit insertion of an alternate gene such as tetK.

A second problem arises, specifically with respect to expression of the S. aureus tetK gene in E. coli. The tetK gene has previously been cloned into an E. coli system and did not confer resistance (8). Thus, evidence indicates that the tetK gene cannot be expressed utilizing the natural S. aureus expression signals, such as the native TTG start codon. Therefore, some manipulation of the tetK gene is necessary to achieve expression in E. coli.

In order to overcome these difficulties, the present invention provides DNA constructs, vectors and E. coli host cells which result in low to moderate levels of proteins encoded therein, particularly heterologous proteins. Such materials are particularly useful in creation of screening assays for inhibitions of tetracycline resistance.

BRIEF DESCRIPTION OF THE FIGURES

FIG. 1A. A schematic representation of the parental plasmid (pCB258) and the four derivatives pCBSal, pGG57, pGG71 and pGG75. Plasmids pCBSal and pCB258 contain the tetA gene, encoding the tetracycline efflux pump from transposon Tn10 of E. coli. Restriction sites found around the start of transcription for tetA present in either pCBSal or pCB258 are depicted. Plasmid pCBSal is deleted for part of the tetracycline repressor operator site located in pCB258, and contains two additional restriction sites (SalI and XhoI). Plasmids pGG57 and pGG71 contain the tetK gene, encoding the tetracycline efflux pump derived from Staphylococcus aureus, present in a 2.0 Kb SalI/HindIII fragment isolated M13 bacteriophage designated GG1 and GG2 respectively. GG1 and GG2 are both generated by oligonucleotide-mediated site-directed mutagenesis of M13 bacteriophage MC71. pGG75 contains a tetC gene, encoding the tetracycline efflux pump derived from pBR322, with a SalI restriction site introduced 5' to the ATG of tetC using Polymerase Chain Reaction. Regulated expression of tetC to high levels of tetracycline resistance involves an uncharacterized regulatory mutation shown by DNA sequence analysis to reside outside of the tetC coding region. The lacI gene encodes the lac repressor which regulates expression of genes under the control of the tac promoter using IPTG.

Figure 1A:
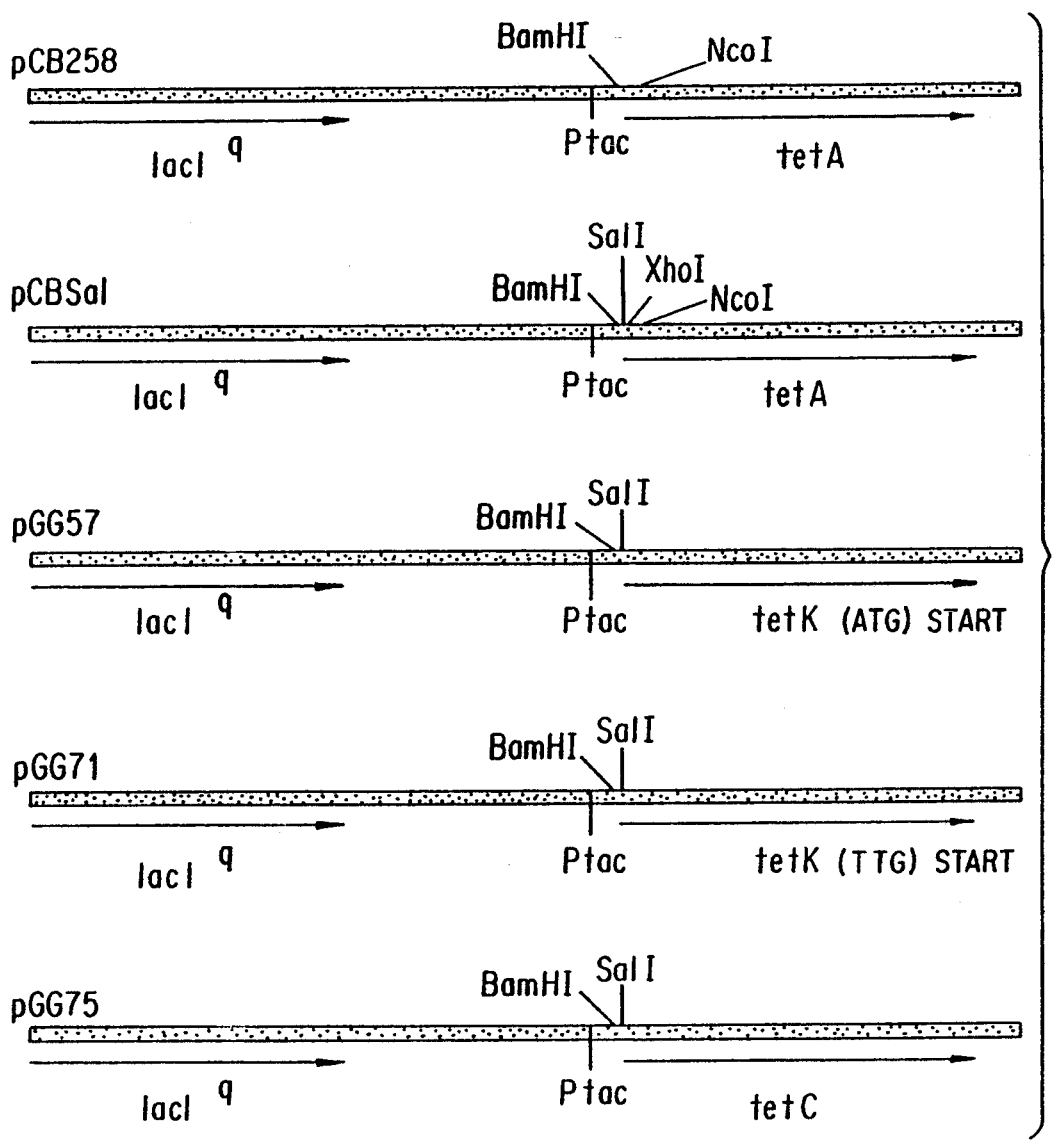
FIGS. 1A and 1B.
Figure 1B:
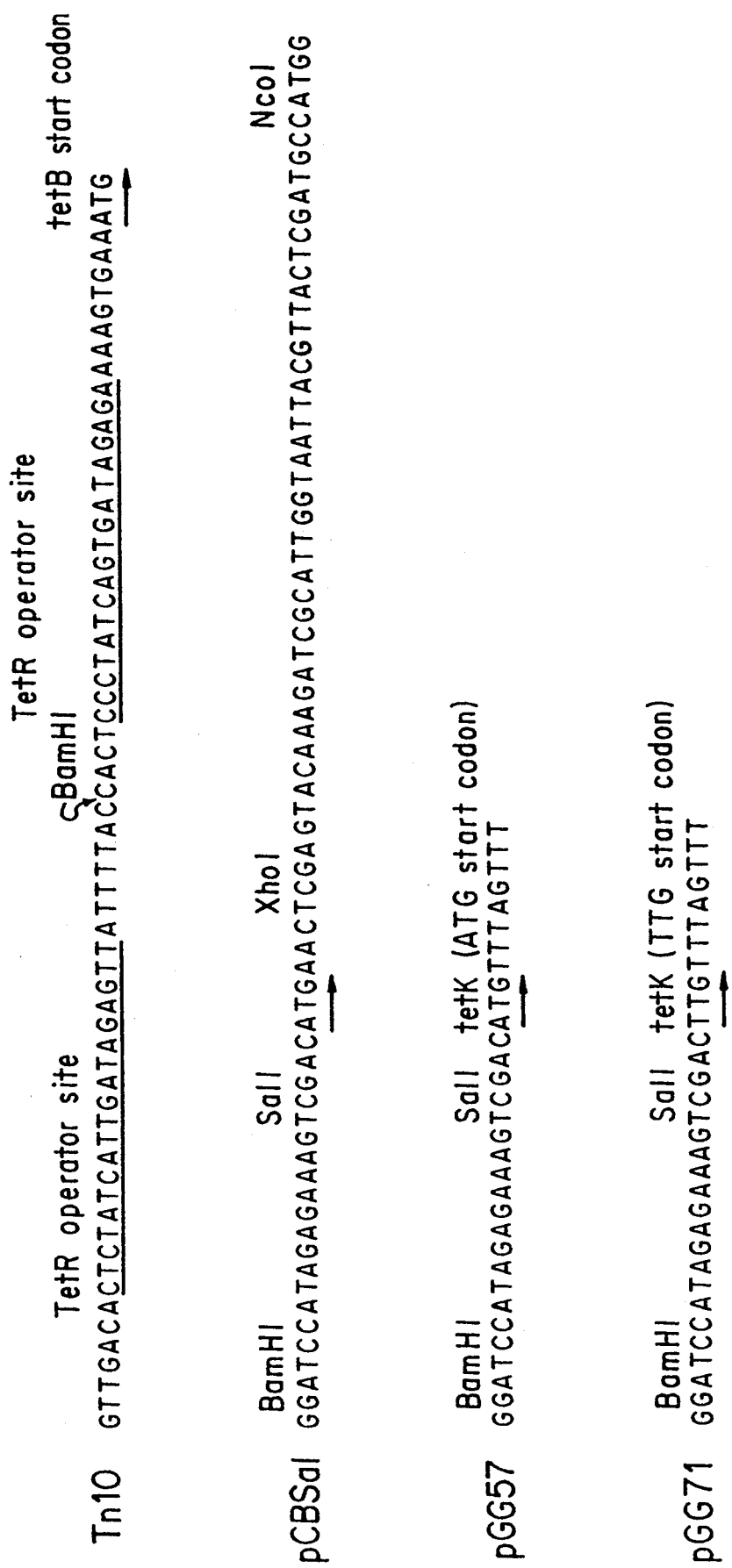

FIG. 1B. The top DNA sequence (SEQ ID NO: 1) is from transposon Tn10 between tetR, encoding the tetracycline repressor, and tetA, encoding the tetracycline efflux pump. The two operator sites found in Tn10 are underlined and the location of the BamHI restriction site is inferred to be present between the two operator sites, from restriction analysis. Although pCBSal contains two unique restriction sites, these changes do not result in alterations of the tetA encoded protein at the amino acid level (SEQ ID NO: 2). The only difference between the two tetK constructs is at the start of translation. The plasmid pGG57 (SEQ ID NO: 3) contains an ATG start codon (underlined) while pGG71 (SEQ ID NO: 4) contains a TTG start codon (underlined). All start codons for each construct are depicted by an arrow.

FIG. 2. Site-directed mutagenesis near the start codon of tetK. The DNA region near the start codon of tetK in the bacteriophage MC71 which was altered using oligonucleotide-mediated site-directed mutagenesis is shown (SEQ ID NO: 5). Oligonucleotide-mediated site-directed mutagenesis requires: (1) a single stranded DNA template one wishes to mutagenize and (2) a short (20–40 bp) complementary oligonucleotide containing within it the desired changes one wishes to introduce into the DNA fragment. The oligonucleotide is allowed to anneal to the complementary single stranded template. Once annealed the 3' OH group of the oligonucleotide serves as a primer for DNA polymerase which is added and results in production of a double stranded product. One of the two strands now contains the alterations introduced by the oligonucleotide primer.

This technique is used with two different oligonucleotide primers (PT1813 and PT1814). The changes in DNA sequence at or near the natural tetK start site are depicted. Both of these oligonucleotide-mediates site-directed mutagenesis reactions resulted in the production of a SalI site 5' to tetK allowing a convenient means to introduce these constructs into pCBSal. In addition to the SalI site, pGG57 contains tetK with an ATG start site (SEQ ID NO: 6) and pGG71 contains tetK with a TTG start site (SEQ ID NO: 7). Other than these changes both of the tetK constructs are identical at the DNA level.

Figure 3A:
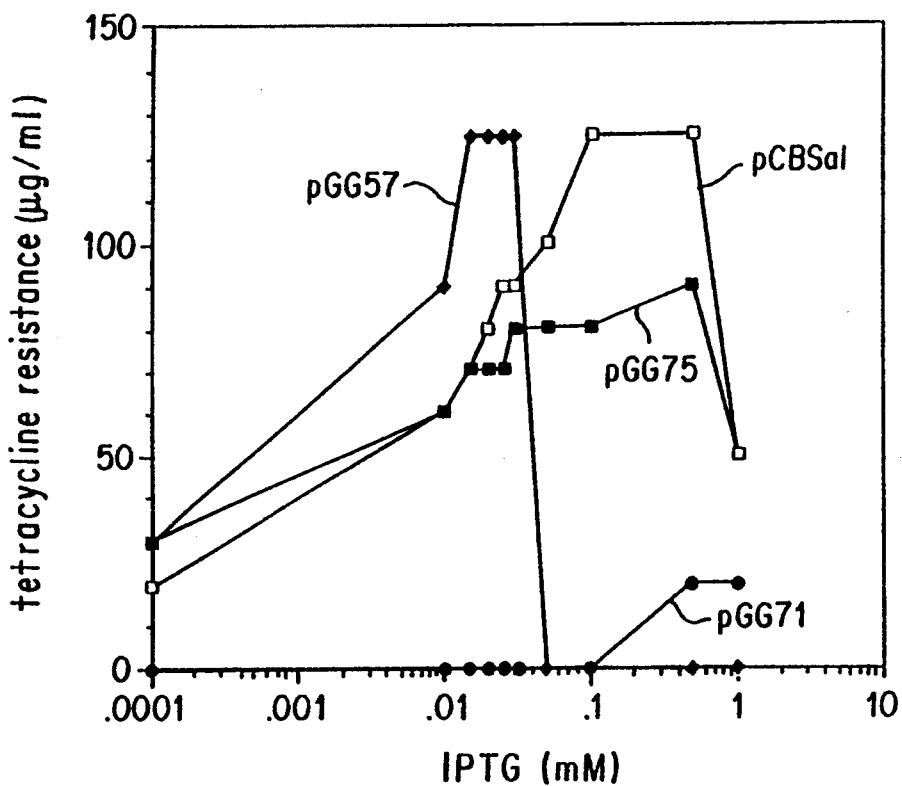

FIG. 3A. The tetracycline resistance profile conferred by the plasmids pCBSal, pGG57, pGG75 and pGG71 in E. coli strain MC1061. Cells are grown in Luria Broth liquid media (8), serially diluted with 0.85% saline, and spread onto agar plates containing increasing concentrations of tetracycline in the presence of increasing concentrations of IPTG. Plates were incubated at 37° C. for 16 hours. The minimum inhibitory concentration of tetracycline required to kill at least 90% loss of colony forming units ($LD_{90}$) is indicated.

Figure 3B:
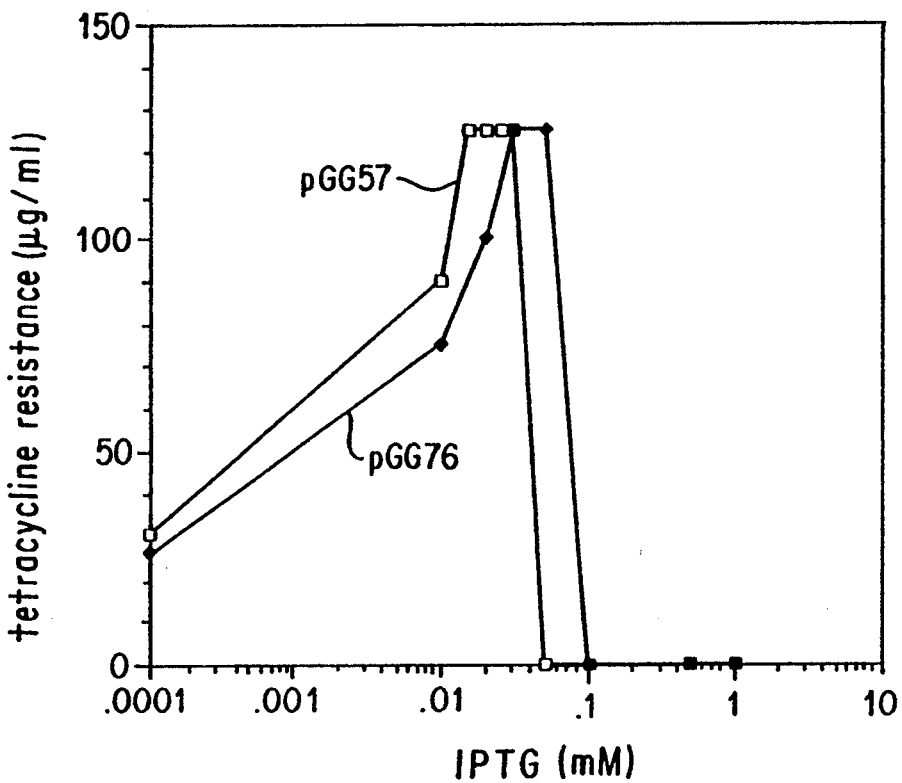

FIG. 3B. The tetracycline resistance profiles of E. coli MC1061 containing pGG57 or pGG76, which both contain tetK and identical regulatory elements, but differ in their plasmid replication region. The procedure used to obtain these profiles is identical to the protocol described in figure legend 3A.

FIG. 4A. The plasmids listed are derivatives of pGG57. The plasmid pGG76 is a pACYC184 derivative of pGG57 containing lacI and tetK. The plasmids pGG77 and pGG84 are deleted for DNA sequence within the tetK coding region.

Figure 4B:
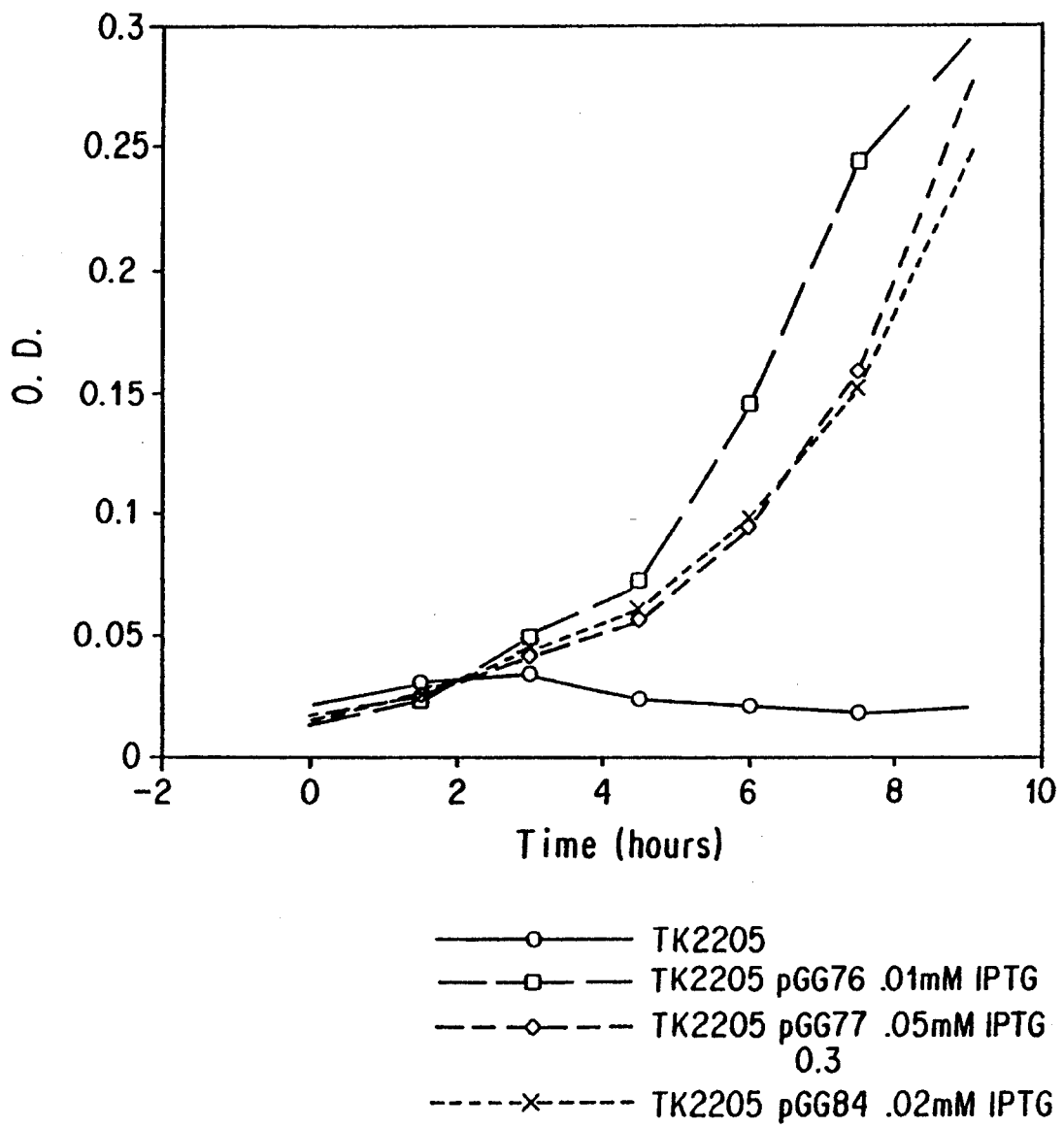

FIG. 4B. The growth curves for E. coli TK2205 grown in minimal media containing 12.5 mM potassium were conducted over a 9 hour period. E. coli TK2205, and E. coli TK2205 containing either pGG76, pGG77 or pGG84. Each culture contains a level of IPTG required for optimum rescue of the potassium uptake deficiency.

SUMMARY OF THE INVENTION

The present invention relates to DNA sequences comprising a portion of a transposon Tn10 tetA gene containing a tetracycline repressor binding site, a 5' region of a ribosome binding site and a translational start codon, the improvement comprising at least partial replacement of the tetracycline repressor binding site and the ribosome binding site by an alternate nucleotide sequence. Throughout the present specification and claims, the term "ribosome binding site" is used in the broad sense as interpreted by Gold and Stormo (15); it is meant to encompass not only a Shine Dalgarno sequence, but also other factors which can affect translation. These include the start codon, the spacing of the Shine Dalgarno from the start codon, the secondary structure of the messenger RNA, the nucleotide sequence of the region 5' to the start codon (5' region herein meaning up to about position $-21$ relative to the start codon), and the sequence of the coding region. Some or all of these factors may be altered by the replacement with the alternate nucleotide sequence in accordance with the present invention. In one embodiment, the alternate nucleotide sequence comprises one or more restriction sites.

In another embodiment, the novel DNA sequences also comprise a coding region for a protein of interest. The coding region may encode a protein native to E. coli, such as a tetracycline efflux pump encoded by tetA. Alternatively, the coding region may encode a protein heterologous to E. coli.

The novel constructs containing a coding region, when expressed in E. coli, yield relatively low levels of the protein encoded thereby. These sequences can be incorporated into E. coli, for example, by transduction using phage P1, or λ phage, or by transformation with a suitable plasmid vector. The microorganisms so produced are useful as research tools for the study of protein expression in cases in which the protein is expected to be toxic to the host cell, or in the study of regulatory proteins, or in screens in which expression of only a small amount of the protein is desirable.

In a preferred embodiment, the microorganisms are used to express genes encoding a tetracycline efflux pump. In a particularly preferred embodiment, the pump is the tetK pump of Staphylococcus aureus. Such microorganisms are useful for screening compounds for the ability to inhibit the tetracycline efflux pump. Methods for such screens are disclosed in copending and cofiled Serial No. [Atty. Docket 31771], entitled "Tetracycline Screening Methods", the contents of which are incorporated herein by reference.

The following terms are used throughout the specification and claims: tetA refers to the gene encoding a tetracycline efflux pump in transposon Tn10; tetC refers to the gene encoding the tetracycline efflux pump of plasmid pBR322; and tetK refers to the gene encoding the tetracycline efflux pump in *Staphylococcus aureus*.

DETAILED DESCRIPTION OF THE INVENTION

The claimed DNA sequences are originally obtained by modification of the BamHI-NcoI fragment found within the plasmid pCB258 gene that encodes the tetracycline pump from transposon Tn10 responsible for tetracycline resistance (the tetA gene). An inducible expression system for tetA regulation has been disclosed by Eckert and Beck (7), as described above. This system, however, may be unacceptable for expression of tetracycline pump genes because it potentially expresses the pump too strongly. Additionally, it lacks a convenient restriction site for cloning of genes other than tetA, and contains a repressor binding site that is incompatible with its use in microorganisms to be used to detect tetracycline pump inhibitors. Therefore, the plasmid, in particular the BamHI-NcaI fragment containing the coding region and a portion of the regulatory region of the tetA gene is investigated in an attempt to provide a sequence which would permit cloning of other genes into the plasmid, as well as permitting low level expression of the genes so cloned.

A schematic diagram of the tetA gene, including a portion of the regulatory region, of Tn10 is provided in FIG. 1B (SEQ ID NO: 1). Tetracycline resistance in enteric bacteria generally is mediated by the transposon Tn10, through the action of two genes. Briefly, the expression of the tetracycline efflux pump gene tetA is regulated by the tetR gene product that can bind to tetR binding sites, located slightly upstream of the tetA coding region (5, 6). The plasmid pCB258 of Eckert and Beck was engineered to achieve controlled expression of the tetA gene by cloning the Tn10 tetA gene behind a tac promoter; expression in this system is under control of the lac repressor encoded on the same plasmid. There was no indication by Eckert and Beck to what extent, if any, either of the tetR repressor binding sites are present on the recombinant plasmid, although restriction analysis indicates that one binding site nearest the tetA coding region remains.

In an attempt to achieve expression of *S. aureus* tetK, the pCB258 plasmid provides a convenient starting point; in particular, attention is focused on the region between the BamHI and NcoI sites of the vector. The details of the sequence of this region are found in FIG. 1B (SEQ ID NO: 2). Inspection shows that there is not a convenient restriction site into which the tetK gene can be cloned. To overcome this problem, a pair of oligomers are synthesized that can hybridize to form a DNA fragment with the desired modifications, and containing a BamHI and NcoI sticky end for cloning into the BamHI and NcoI sites of the vector by standard cloning methods (9). One strand is illustrated in FIG. 1B (labelled "pCBSal"). The substitution of this fragment in the vector results in the introduction of two unique restriction sites, a SalI site upstream and adjacent to the initiation codon, and an XhoI site within the coding region, which does not alter the amino acid sequence of the tetA protein. The changes including the SalI site have an unexpected effect. When this vector is used to express tetA in *E. coli*, the new sequence weakens expression of tetA. In the absence of IPTG, strain MC1061, carrying pCB258 confers resistance to 40 μg/ml of tetracycline whereas MC1061 carrying plasmid pCBSal confers resistance to just 20 μg/ml of tetracycline. Furthermore, cell death associated with gene expression of the strain containing pCB258 occurs when 0.2 mM IPTG is present, whereas MC1061 containing pCBSal is not killed until 1 mM IPTG is added. This suggests that the change alters the strength of the tetA ribosome binding site, rendering it less efficient, and/or alters the stability of the mRNA.

This construct is then used to attempt expression of the *S. aureus* tetK gene in *E. coli*. Since the unmodified tetK gene, when present in *E. coli*, does not confer resistance, some alteration is required. To achieve expression in *E. coli*, the tetK gene, in bacteriophage M13, is modified to contain a SalI site immediately 5' to the start site for cloning purposes. Additionally, as a convenience to facilitate expression in *E. coli*, the normal tetK TTG start codon is mutagenized to ATG. The tetK gene thus modified is then ligated into the pCBSal vector.

The plasmid pGG57 is used to transform *E. coli* and to test for tetK expression. The effect of the apparently weakened ribosome binding site, balanced by the presence of an *E. coli* ATG start codon, results in a strain that confers in the absence of inducer a modest level of tetracycline resistance of about 25 μg/ml, and therefore produces a low level of the *Staphylococcus aureus* tetK gene product.

Although *E. coli* with plasmids derived from pCBSal express suitably low levels of the protein, it is possible to decrease the level of expression even further by removing the strong tac promoter preceding the tet gene. In both the parental pCB258 and plasmid pCBSal, expression is regulated by this promoter. However, substantial expression occurs from pCB258, and to a lesser extent, from pCBSal, even in the absence of inducer. Expression can be reduced further by cloning the gene of interest and its ribosome binding site, but not its transcriptional start signals, into another plasmid. The position in the new plasmid is preferably not within a gene that is actively transcribed. Plasmids of this type are particularly useful in expression of tetracycline efflux pump genes, but, as one skilled in the art will readily recognize, they can also be used in expression of any heterologous gene in *E. coli*. Other genes for which such a low level expression system might be useful include, for example, regulatory proteins in screens or proteins which are toxic to the cells in large amounts.

In the context of developing a screening microorganism to detect tetracycline pump inhibitors, this type of strain is ideal. Other tetracycline-pump containing organisms, for example strains carrying transposon Tn10, have a number of disadvantages in this type of system. For example, Tn10 confers a high level of resistance to tetracycline, and thus, there are many pumps to inhibit before a signal might be detected in a fully tetracycline resistant strain. Also, the tetA gene of Tn10 is regulated; inhibition of efflux pumps will result in an increased synthesis of new efflux pumps, as a response to the increased intracellular level of tetracycline, so that the effect of an inhibitor will be minimized by a fully tetracycline resistant strain. Transposon Tn10 also contributes the repressor gene tetR, as well as the tetA gene; increased expression of the repressor may cause diminished sensitivity (10). Even pCB258, the Eckert and Beck plasmid, which has been modified in such a way that expression can be controlled to some extent, still has its disadvantages. A low, constitutive level of tetA expression is optimal for a screening organism to detect inhibitors of the tetracycline efflux pump, a task to which the Eckert and Beck system is not ideally suited, for several reasons. First, the level of tetA expression in strains containing pCB258 is still too high (MIC=50 µg/ml, in the absence of IPTG) for optimal use in screening for pump inhibitors. Second, lactose, which would induce expression of tetA on plasmid pCB258, might be present within fermentation broths to be screened, interfering with the screen. Further, restriction analysis of plasmid pCB258 indicates that one of the two operator binding sites of the tet regulatory region is present in plasmid pCB258. In a screening organism utilizing the tet regulatory elements and therefore containing the tetR gene, a low, constitutive level of tetA expression could not be achieved. Finally, there is no convenient restriction site in the appropriate region to permit insertion of an alternate gene, such as tetK.

In the context of using low expression systems for other studies, the regulated expression of tetA, tetC and tetK in an isogenic host allows for the careful comparison of gene products. For example, one may observe that one strain of bacteria containing one tetracycline resistance determinant is more sensitive to a particular tetracycline than a different microorganism containing a second tetracycline resistance determinant. It is difficult to conclude whether differences are attributable to a determinant or a strain. The present invention allows careful comparisons between three distinct tetracycline efflux pumps in the identical genetic background, to test the hypothesis that different pumps have distinct substrate specificities (11). It shows that the tetA pump from transposon Tn10 does not differ markedly from the related tetC pump, whereas the tetK pump, from S. aureus does appear to exhibit a different substrate specificity. It also permits investigation of whether the tetK pump of S. aureus has the capacity to facilitate entry of potassium ions into the cell, as the tetC pump does (12), but not the tetA pump. These experiments are only possible to conduct in E. coli strains specifically deficient in potassium uptake (12), which are not available in S. aureus. It is determined that the tetK pump was capable of facilitating entry of potassium ions. It also allows investigation of whether hybrid pump proteins can function by utilizing the present regulated, low expression system. It is also found that at least some hybrid tetC-tetA pumps can function, in contrast to previous studies (13). Therefore the low expression system is a valuable asset, both in constructing screening organisms as well as in studying the function of these proteins that have lethal effects if overexpressed.

It will be apparent that certain modifications within the specific pCBSal sequence can be made without altering the overall effect on the useful characteristics of the sequence. For example, it is contemplated that the SalI site may be replaced with any restriction site. It will also be understood that, depending on the gene to be expressed, and the desired level of expression, alternate promoters can be used as well, for example, E. coli trp, or λ PL. Also, as will be shown in the following examples the invention is not limited to use of a particular plasmid, as expression can be readily achieved on unrelated plasmids, and the modifications which may be required to insert the desired sequence into other plasmids, i.e., modification of restriction sites, are within the skill of the art given the disclosure of the present specification. Also, although the constructs have been developed in association with the expression of tetracycline efflux pump genes, it is apparent that any gene for which low expression in E. coli is desirable can be used in place of the tetA or tetK genes.

The practice of the invention is further illustrated by the following non-limiting examples.

EXAMPLES

Construction of Plasmid pCBSal

A pair of synthesized complementary oligomers shown below (SEQ ID NO: 10 and 17 respectively), containing BamHI and NcoI ends, is ligated into the large BamHI/NcoI fragment of pCB258 (7), using the standard ligation conditions (9). GATC-CATAGAGAAAGTCGACATGAACTCGAG-TACAAAGATCGCATTGGTAATTACGTTACT-CGATGC GTATCTCTTTCAGCTGTACTT-GAGCTCATGTTTCTAGCGTAACCATTAATG-CAATGAGCTACGGTAC Plasmid pCBSal is deleted for a tetracycline operator binding site found in pCB258, and contains two unique restriction sites; a SalI site immediately 5' to the start codon tetA and an XhoI restriction site in the coding region of tetA which does not alter the amino acid sequence encoded by the gene. The BamHI site is also unique in pCBSal.

Construction of Expression Vectors Containing tetK

A pCBSal derivative that expresses the tetK gene in E. coli is constructed in two steps. First, the tetK gene in the M13 bacteriophage, MC71 (8), is mutagenized using oligonucleotide-mediated site-directed mutagenesis according to Kunkel, et al. (14). The oligomer 5'-CCTCAAGTAAAGAGGTCGACATGTTAGTT-TAG-3' (SEQ ID NO: 8) is used to alter the naturally occurring tetK start codon to ATG, and to introduce a SalI restriction site just upstream of the new start codon. Then the RFI phage DNA containing the modified tetK gene is digested with SalI/HindIII and ligated into the large fragment generated when pCBSal is digested with SalI/HindIII, resulting in plasmid pGG57. An isogenic plasmid containing the original TTG start codon of the tetK gene, called pGG71, is also constructed in two steps. The oligomer 5' AAGAGGT-CGACTTGTTTAGTTAAG 3' (SEQ ID NO: 9) is used to introduce a SalI restriction site adjacent to the natural (TTG) translational start codon for tetK. Plasmid pGG71 is constructed in the manner outlined above. The sequences of all phage constructs are verified using DNA sequence analysis according to standard procedures (9).

The tetK gene is cloned onto an alternative expression vector by digesting plasmid pGG57 with ScaI and HindIII enzymes, and ligating the 2.7 Kb fragment to the large fragment generated by digesting plasmid pA-CYC184 with HindIII and HindIII enzymes. The resulting recombinant, designated pGG76, contains the lacI gene, the tac promoter, followed by the tetK gene containing the ATG initiation codon.

The tetC gene encoding the tetracycline efflux pump from plasmid pBR322 is transferred into this expression system by using polymerase chain reaction to engineer a SalI site just prior to the ATG start codon, using standard techniques (9). The resulting plasmid is digested with SalI and NheI enzymes, and the small fragment containing the 5' end of the tetC coding region is isolated. The 3' end of the tetC is isolated by digesting pBR322 with AvaI enzyme, filling in with Klenow enzyme, and digesting with NheI enzyme. The entire tetC coding region is ligated into the expression system by means of a three-way ligation, in which the expression vector is prepared by digesting with HindIII, filling in, and digesting with SalI enzyme. (A two-way ligation is not straightforward due to the presence of a SalI site within the tetC gene.) The plasmid containing the entire tetC gene is isolated following transformation of strain MC1061, selecting for ampicillin resistance. Standard techniques are used (9).

Tetracycline resistance of plasmid pGG57 within strain MC1061 is 15 µg/ml, even when high levels of IPTG are added to the medium. The level of tetracycline resistance is at least five times lower than tetracycline resistance conferred by plasmid pBR322, indicating that the optimal level of expression is not attained. Therefore mutants are selected that can survive the presence of 100 µg/ml of tetracycline in LB agar that also contained 0.1 mM IPTG, to permit some induction. One mutant derivative, containing plasmid pGG75, is isolated and used in subsequent studies. The mutation is determined to be located on the plasmid, since transformants breed true for high tetracycline resistance. The possibility of a mutation within the tetC coding region is eliminated by sequencing the entire tetC coding region, and finding only wild type sequence, using standard techniques (9).

Determination of tetracycline resistance

E. coli strain MC1061 containing plasmids pCBSal, pGG57, pGG71, pGG75 or pGG76, are tested for tetracycline resistance by growing overnight cultures in Luria Broth (2) containing 50 µg/ml of ampicillin. A 1:50 dilution of each overnight culture is inoculated into fresh L-A broth. Exponentially growing cells are serially diluted in 0.85% saline such that each plate is inoculated with 200-500 cells. The cells are spread on L-agar (pH 6.8-7.0) containing ampicillin (50 µg/ml), containing a range of IPTG and tetracycline concentrations (0.001 mM-1.0 mM IPTG and 0-200 µg/ml of tetracycline). The plates are incubated at 37° C. for 18-20 hours and the minimum inhibitory concentration (MIC) is determined as the concentration of tetracycline preventing at least 90% of the cells from forming colonies (LD 90). A comparison of pCBSal, pGG57, pGG75 and pGG71 is shown in FIG. 3A. Plasmid pCBSal confers the same level of tetracycline resistance when compared with pCB258; however, pCB258 confers higher resistance in the absence of IPTG (MIC=50). Furthermore, just 0.1 mM IPTG is sufficient to kill cells containing pCB258, whereas 1 mM IPTG is necessary to kill cells containing pCBSal. Thus, an alteration in the ribosome binding site is indicated. Plasmid pGG57, containing the tetK gene with an ATG start site, also confers resistance when grown at low levels of IPTG, and like expression of tetA, further induction causes cell death. Plasmid pGG71 containing a TTG start codon, confers extremely low levels of resistance, which occurs only at high IPTG levels. This result indicates the importance of the ATG start site in expression of the tetK gene in E. coli.

The results of pGG76 tetK expression are shown in FIG. 3B. Plasmid pGG76 contains the origin of replication of pACYC184, whereas plasmid pGG57 relies on pBR322 origin. As the figure shows, upon induction with IPTG, E. coli MC1061 carrying pGG76 shows a similar tetracycline resistance profile to MC1061 carrying pGG57, except that more IPTG is required to achieve maximum tetracycline resistance. This is consistent with the fact that pACYC184 derivatives are present in lower copy number than pGG57, and therefore might be expected to require more IPTG to confer full resistance. Overall, these results show that the regulatable expression of tetK can be used in unrelated plasmid types.

Construction of an Unregulated tetK Expression Plasmid

The plasmids pGG57, pGG71, pGG75, pGG76, and pCBSal all are useful in lower level expression of the tet genes in that the feature of regulation by the tetR gene product is removed, and the ribosome binding site is altered so as to weaken translation. However, the plasmids all contain a regulatory element, the lacI gene, which regulates the inducible tac promoter. For purposes of the screening microorganism, it may be desirable to eliminate this final level of regulation, so that the tetK gene is expressed at a low constitutive level. To this end, a derivative of plasmid pBT401 (10) containing the tetA gene of transposon Tn10 is constructed by digesting plasmid pCBSal with SmaI restriction enzyme and ligating the small fragment into plasmid pBT401 that is digested with BamHI enzyme and filled in with Klenow enzyme as described (9). In the construct that confers tetracycline resistance, the gene is in the same orientation as the kanamycin resistance (aph) gene, determined by restriction analysis. When the gene is in the opposite orientation, no tetracycline resistance is detected. An isogenic plasmid containing the tetK gene of S. aureus is similarly constructed using plasmid pGG57 as the source of tetK.

These plasmids are used to transform an appropriate E. coli strain for use in screening assays for tetracycline efflux pump inhibitors.

Substrate Specificity of Tetracycline Efflux Pumps

Previous studies suggest that tetracycline efflux pumps vary in their ability to recognize and pump out different tetracyclines (11). This interpretation is limited by alternative explanation. It is possible, for instance, that differences can be attributed to susceptibility of the host strain. Furthermore, if one efflux pump confers stronger resistance to tetracycline, it is difficult to distinguish whether low-level resistance to a derivative, such as minocycline, is attributable to the ability of the pump to recognize minocycline, as opposed to its enhanced ability to pump all tetracycline substrates. It is even possible that the "better" pump is simply less lethal, and tolerated in greater numbers, rather than a more efficient pump. In order to rule out other possibilities and to look at different substrates as the only variable, the abilities of tetA-, tetC- and tetK-encoded pumps to confer resistance to a single host strain MC1061 to a variety of tetracyclines are studied using the present low-level regulated system (Table 1). Using this expression system, it is shown that the closely related efflux systems, tetA and tetC, do not show any marked differences in substrate specificities to different tetracycline analogs. Furthermore, when the IPTG concentration is reduced for MC1061 carrying tetA, so that the tetracycline resistance is the same as the tetC strain, then the minor differences in resistance to other tetracyclines disappear (data not shown). In contrast the tetK efflux system does show differences in its ability to pump out the tetracycline derivatives minocycline, doxytetracycline, and 6-demethyl-6-deoxytetracycline (Table 1). Thus the low-level, regulated expression system allows the ruling out of alternative explanations, and to determine true differences in substrate specificity among tetracycline efflux pumps.

TABLE 1

MIC (LD 90) of Maximally Induced tetA, tetK and tetC

|  | pCBSal | pGG57 | pGG75 |
|---|---|---|---|
| Tetracycline | 150 | 175 | 100 |
| Minocycline | 14 | 4 | 8 |
| AnhydroTc | 3 | 2 | 2 |
| OxyTc | >300 | 250 | 300 |
| DoxyTc | 40 | 7 | 20 |
| ChloroTc | 50 | 40 | 40 |
| 6-demethyl 6-deoxyTc | 20 | 7 | 20 |

*E. coli* MC1061 containing either pGG57, pCBSal or pGG75 are used to determine the MIC (LD 90) for tetracycline as well as six tetracycline analogs. Each plasmid requires a different level of IPTG for maximum induction. MIC studies are performed in the presence of 0.01 mM IPTG for *E. coli* MC1061 containing pGG57. An IPTG level of 0.5 mM is required for optimum induction of *E. coli* MC1061 containing pGG75. *E. coli* MC1061 containing pCBSal requires an IPTG level of 0.1 mM IPTG for maximum induction. All of these MIC studies are done in duplicate.

Potassium uptake as an Additional Measure of Expression of Tetracycline Efflux Pumps In addition to pumping tetracycline out of the host cell, the tetC pump, but not the tetA pump, has the ability to pump potassium into *E. coli*. In order to see this phenotype, a host *E. coli* strain that is crippled for potassium uptake due to two mutations, such as TK2205, must be used (12). Our expression system, and the adaptations that result in tetK expression in *E. coli*, permits the determination that the tetK pump also has the capacity to facilitate potassium entry. When tetK is induced with IPTG, in minimal medium containing a low concentration of potassium, then good growth is observed, when either plasmid pGG57 or plasmid pGG76 are used (FIG. 4). For the tetC gene, potassium uptake and tetracycline efflux are independent functions; in fact, deletion derivatives that are incapable of any efflux activity still maintain the ability to pump in potassium (12). For the tetK pump as well, potassium uptake can occur when just a fragment of the gene is expressed, in the absence of tetracycline efflux activity (FIG. 4). In order to generate the constructs outlined in FIG. 4a, plasmid pGG76 is digested with KpnI and SpeI restriction enzymes and blunt ends are created which are ligated to produce plasmid pGG77. Similarly, plasmid pGG76 is digested with EcoNI enzyme, which cuts twice within the plasmid, and religated to form plasmid pGG84, using standard cloning techniques (9). Both derivative plasmids confer to strain TK2204 the ability to grow in the presence of low levels of potassium. Thus for both of these pumps, the ability to pump potassium is localized to the first third of the gene. In the present state of the art, these studies cannot be conducted using the native host species, *S. aureus*, because potassium uptake mutants are not available.

The Construction of Hybrid Tetracycline Efflux Pumps

The regulated expression system allows construction of hybrid pumps, in order to investigate whether activities, such as potassium uptake, substrate-specificity, or strong resistance can be localized to a domain of the pump. To this end, a hybrid gene is constructed encoding the first 47 amino acids of the tetC gene and the remainder of the gene encoding the tetA gene, using polymerase chain reaction and oligonucleotide-mediated site-directed mutagenesis, as well as restriction digestion, and ligation as described (9). This hybrid gene, ligated into plasmid pGG75, encodes a protein that confers tetracycline resistance to the host strain MC1061. Thus, a hybrid protein can function for tetracycline efflux, in contradiction to published reports (13), providing the proper level of expression is attained. Other hybrid genes are also constructed, with the aim of determining if protein domains with specific function can be identified.

The following biological materials have been deposited with the American Type Culture Collection, 12301 Parklawn Drive, Rockville, Md., on Dec. 3, 1991, and have been given the designated accession numbers. These are also available in the culture collection of American Cyanamid Company, Lederle Laboratories, Pearl River, N.Y.

| Plasmid | Accession No. |
|---|---|
| *E. coli* MC1061/pCBSal | ATCC 68855 |
| *E. coli* MC1061/pGG57 | ATCC 68856 |

BIBLIOGRAPHY

1. McMurray, L. M., R. E. Petrucci, Jr., and S. B. Levy. 1980. Active efflux of tetracycline encoded by four genetically different tetracycline resistance elements in *Escherichia coli*. Proc. Natl. Acad. Sci. 77:3974–3977.
2. Mojumdar, M. and S. A. Khar, 1988. Characterization of the tetracycline resistance gene of plasmid pT181 of *Staphylococcus aureus*. J. Bacteriol. 170:5522–5528
3. Coleman, D. C., and T. J. Foster. 1981. Analysis of the reduction in expression of tetracycline resistance determined by transposon Tn10 in the multicopy state. Mol. Gen. Genet. 182:171–177.
4. Moyed, J. S., T. T. Nguyen, and K. P. Bertrand. 1983. Multicopy Tn10 tet plasmids confer sensitivity to induction of tet gene expression. J. Bacteriol. 155:549–556.
5. Bertrand, K. P., K. Postle, L. V. Wray, Jr., and W. S. Reznikoff. 1983. Overlapping divergent promoters control expression of Tn10 tetracycline resistance. Gene. 23:149–156.
6. Hillen, W., K. Schollmeier, and C. Gatz. 1984. Control of expression of the Tn10-encoded tetracycline resistance operon II. Interaction of RNA polymerase and TET repressor with the tet operon regulatory region. J. Mol. Biol. 172:185–201.
7. Eckert, B., and C. F. Beck. 1989. Overproduction of Transposon Tn10-Encoded Tetracycline Protein Results in Cell Death and Loss of Membrane Potential. J. Bact. 171:3557–3559.
8. Richard Novick, personal communication.
9. Sambrook, J., E. F. Fritsch and T. Maniatis. 1989. Molecular Cloning; a laboratory manual (second edition). Cold Spring Harbor Laboratory Press, Cold Spring Harbor, N.Y.
10. Bertrand, K. P., K. Postle, L. V. Wray, Jr., and W. S. Resnikoff. 1984. Construction of a single-copy promoter vector and its use in analysis of regulation of the transposon Tn10 tetracycline resistance determinant. J. Bacteriol. 158:910–919.
11. Chopra, I., K. Hacker, Z. Misulovin and D. M. Rothstein. 1990. Sensitive biological detection method for tetracycline using a tetA-lacZ fusion system. Antimicrob. Agents Chemoth. 34:111–116.
12. Dosch, D. C., F. F. Salvacion and W. Epstein. 1984. Tetracycline Resistance Element of pBR322 Mediates Potassium Transport. J. Bacteriol 160:1188–1190.
13. Rubin, R. A. and S. Levy. 1990. Interdomain Hybrid Tet Proteins Confer Tetracycline Resistance Only When They are Derived from Closely Related Members of the tet Gene Family. J. Bacteriol. 172:2303–2312.
14. Kunkel, T. A., J. D. Roberts and R. A. Zakour. 1987. Rapid and efficient site-specific mutagenesis without phenotypic selection. Methods Enzymology. 154:367.
15. Gold L. and G. Stormo. 1987. *Eschericia coli* and *Salmonella Typhimurium:* Cellular and Molecular Biology. F. C. Niedhard (ed.) American Society of Microbiology. Washington D.C. Vol. 2:1302–1307.

---

What we claim is:

1. An isolated DNA molecule comprising pCBSal or pGG57 translation initiation regions as depicted in FIG. 1B, SEQ ID NO. 2 and SEQ ID NO. 3, linked to a coding region selected from the group consisting of a tetA gene of transposon Tn10 and tetK gene of *S. aureus* encoding a tetracycline efflux pump protein.

2. A vector comprising the DNA molecule off claim 1.

3. The vector of claim 2 which is a plasmid.

4. An *E. coli* host cell comprising the DNA molecule of claim 1.

5. The *E. coli* host cell of claim 4 capable of expressing a Staphylococcus tetK gene.

* * * * *

UNITED STATES PATENT AND TRADEMARK OFFICE
CERTIFICATE OF CORRECTION

PATENT NO. : 5,384,259

DATED : January 24, 1995

INVENTOR(S) : David M. Rothstein et al.

It is certified that error appears in the above-indentified patent and that said Letters Patent is hereby corrected as shown below:

Column 8, line 15: Change "17" to --11--.

Signed and Sealed this

Fifth Day of September, 1995

Attest:

BRUCE LEHMAN

*Attesting Officer*      *Commissioner of Patents and Trademarks*

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
        ( A ) LENGTH: 66 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

```
GTTGACACTC  TATCATTGAT  AGAGTTATTT  TACCACTCCC  TATCAGTGAT  AGAGAAAAGT      60

GAAATG                                                                      66
```

( 2 ) INFORMATION FOR SEQ ID NO:2:

( i ) SEQUENCE CHARACTERISTICS:
        ( A ) LENGTH: 72 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

```
GGATCCATAG  AGAAAGTCGA  CATGAACTCG  AGTACAAAGA  TCGCATTGGT  AATTACGTTA      60

CTCGATGCCA  TG                                                              72
```

( 2 ) INFORMATION FOR SEQ ID NO:3:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

```
GGATCCATAG  AGAAAGTCGA  CATGTTTAGT                                          30
```

( 2 ) INFORMATION FOR SEQ ID NO:4:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

GGATCCATAG AGAAAGTCGA CTTGTTTAGT                30

( 2 ) INFORMATION FOR SEQ ID NO:5:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:5:

GTAAAGAGGT AAAATTGTTT AGTTTA                    26

( 2 ) INFORMATION FOR SEQ ID NO:6:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:6:

GTCGACATGT TTAGTTT                              17

( 2 ) INFORMATION FOR SEQ ID NO:7:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:7:

GTCGACTTGT TTAGTTT                              17

( 2 ) INFORMATION FOR SEQ ID NO:8:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:8:

CCTCAAGTAA AGAGGTCGAC ATGTTAGTTT AG             32

( 2 ) INFORMATION FOR SEQ ID NO:9:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:9:

AAGAGGTCGA CTTGTTTAGT TAAG                      24

( 2 ) INFORMATION FOR SEQ ID NO:10:

( i ) SEQUENCE CHARACTERISTICS:
        ( A ) LENGTH: 67 base pairs (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:10:

```
CGTAGCTCAT TGCATTAATG GTTACGCTAG AAACATGAGC TCAAGTACAG CTGAAAGAGA        60

TACCTAG                                                                  67
```

(2) INFORMATION FOR SEQ ID NO:11:

(i) SEQUENCE CHARACTERISTICS:
        (A) LENGTH: 67 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:11:

```
CATGGCATCG AGTAACGTAA TTACCAATGC GATCTTTGTA CTCGAGTTCA TGTCGACTTT        60

CTCTATG                                                                  67
```